United States Patent [19]

Fukasawa

[11] Patent Number: 4,765,959

[45] Date of Patent: Aug. 23, 1988

[54] BLOOD CIRCULATING CIRCUIT FOR MEMBRANE-TYPE ARTIFICIAL LUNG, AND RESERVOIR FOR USE IN BLOOD CIRCULATING CIRCUIT

[75] Inventor: Hiromichi Fukasawa, Funabashi, Japan

[73] Assignee: Terumo Kabushiki Kaisha, Tokyo, Japan

[21] Appl. No.: 797,776

[22] Filed: Nov. 12, 1985

Related U.S. Application Data

[63] Continuation of Ser. No. 439,422, Nov. 5, 1982, abandoned.

[30] Foreign Application Priority Data

Nov. 13, 1981 [JP] Japan ................. 56-180983

[51] Int. Cl.$^4$ .............................................. A61M 1/18
[52] U.S. Cl. .............................. 422/48; 210/321.78; 422/44
[58] Field of Search ...................... 422/44, 48, 45; 210/321.4

[56] References Cited

U.S. PATENT DOCUMENTS

| | | | |
|---|---|---|---|
| 3,853,479 | 12/1974 | Talonn et al. | 422/47 |
| 3,907,504 | 9/1975 | Hammond et al. | 422/48 |
| 3,927,980 | 12/1975 | Leonard | 422/48 |
| 4,026,669 | 5/1977 | Leonard et al. | 422/44 |
| 4,466,804 | 8/1984 | Hino | 422/44 |

FOREIGN PATENT DOCUMENTS

| | | |
|---|---|---|
| 5866 | 5/1963 | European Pat. Off. . |
| 1148354 | 5/1963 | Fed. Rep. of Germany . |
| 2501552 | 7/1975 | Fed. Rep. of Germany . |
| 55-180536 | 12/1980 | Japan . |

OTHER PUBLICATIONS

Kishi et al., Artificial Organs (vol. 6, No. 6, 1977) pp. 1 & 2, 270, 271 and 498.
SciMed Life Systems, Inc., The SciMed System, (SCI-1/78-6302) pp. 1-5.
Kimura et al., Artificial Organs (vol. 9, No. 2, 1980) pp. 1-3, 558-561 & 650.
The Annals of Thoracic Surgery, Published by Little, Brown & Co., Boston, Mass., vol. 26, Jul.-Dec., 1978, pp. 1-4 & 54-60.

Primary Examiner—Michael S. Marcus
Attorney, Agent, or Firm—Frishauf, Holtz, Goodman & Woodward

[57] ABSTRACT

A sealed-type flexible reservoir constituting part of the blood circulating circuit of a membrane-type artificial lung is regulated to a specified volume by a pair of opposing planar restricting members, thereby specifying the amount of blood circulating through the circuit. The reservoir comprises a vessel provided at its upper portion with deaeration ports, a blood inflow tube having two or more side apertures for communication with the interior of the vessel, and a blood outflow port for guiding blood exiting from the vessel. The side apertures are located at a position higher than the blood outflow port, with the blood inflow tube and blood outflow port being spaced away from each other by a predetermined distance, Accordingly, air bubbles carried into the reservoir by the flowing blood may be removed from the deaeration ports without being drawn out through the blood outflow port.

10 Claims, 12 Drawing Sheets

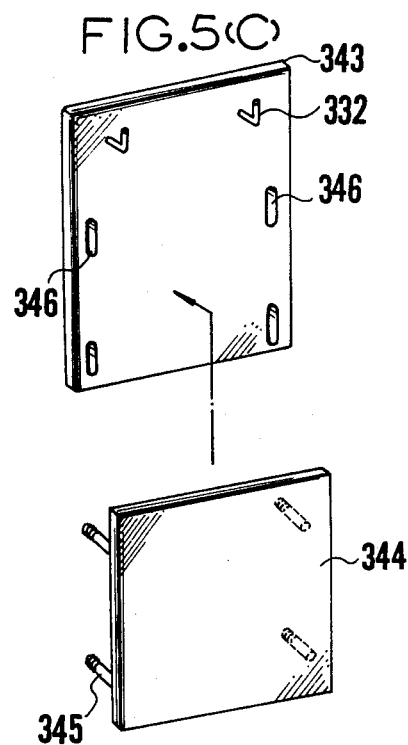
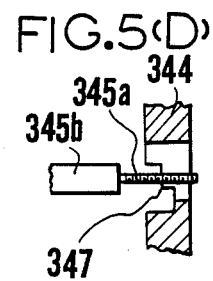
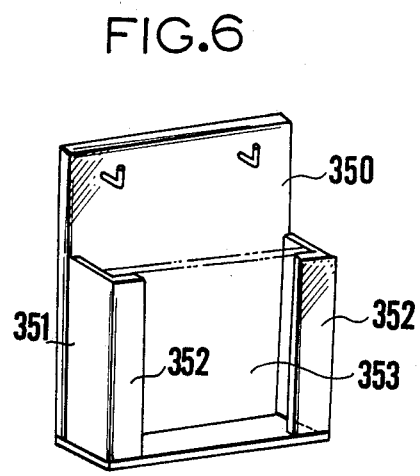
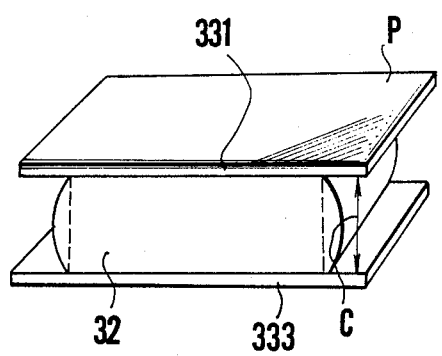

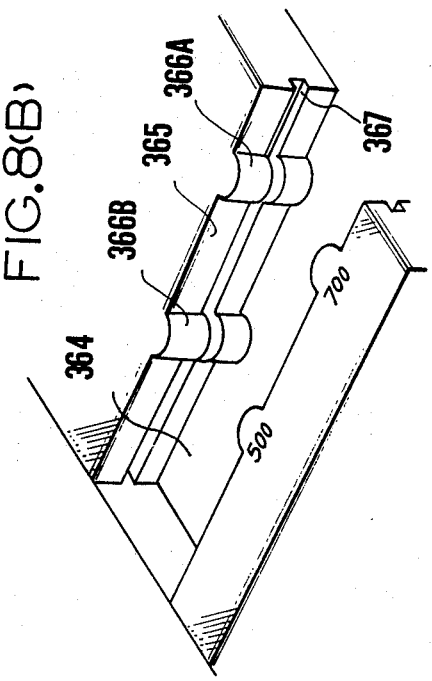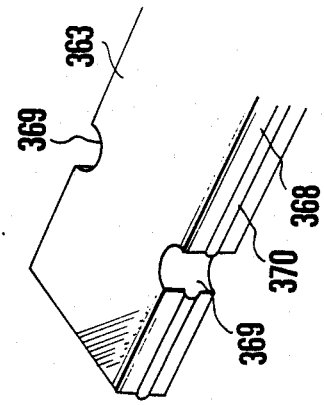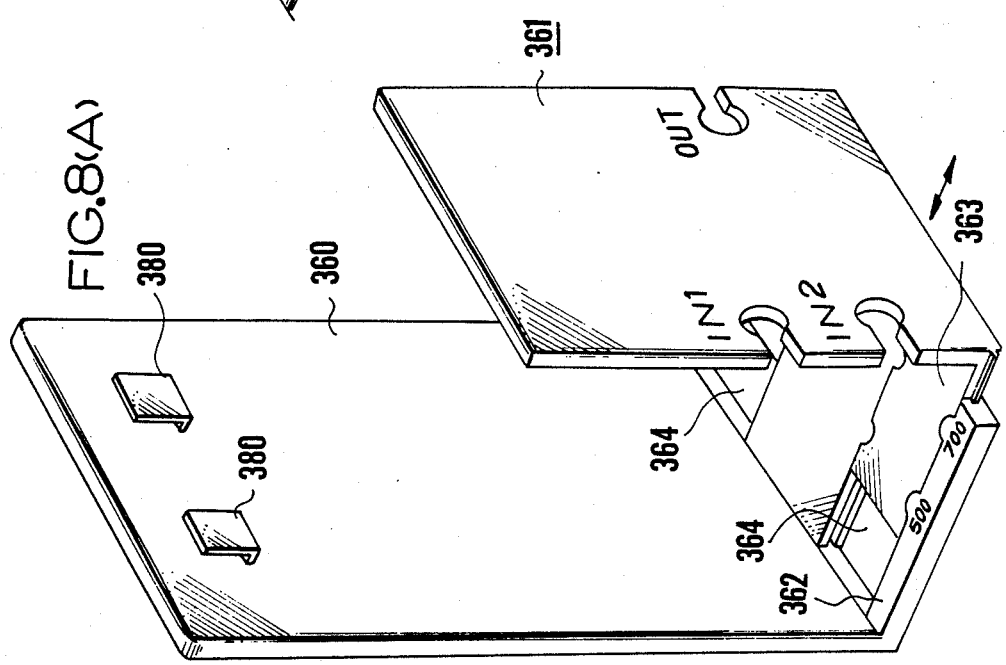

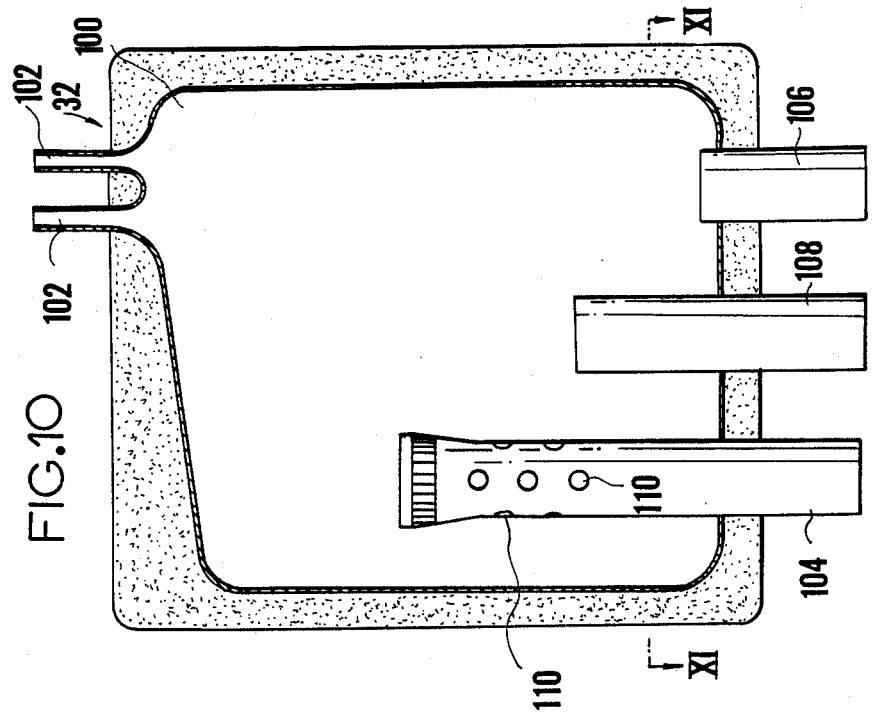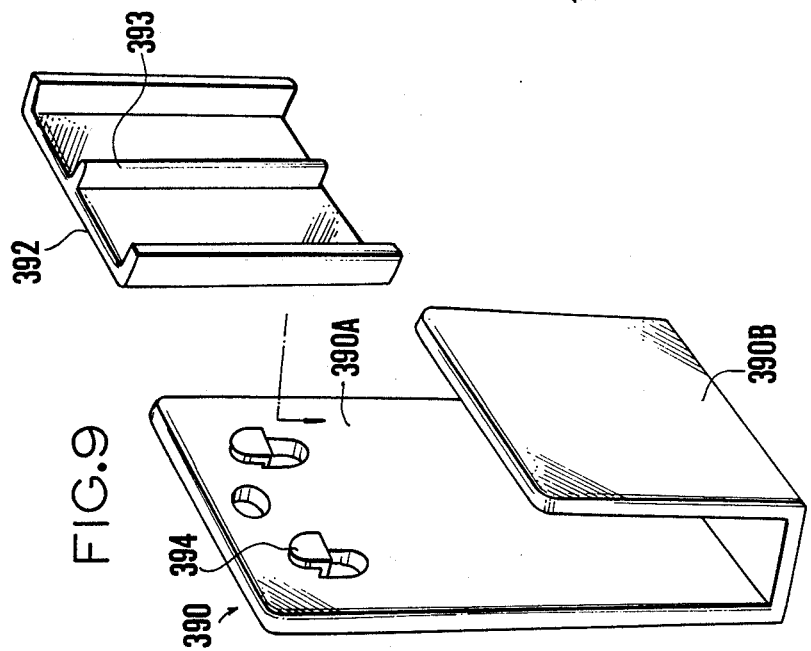

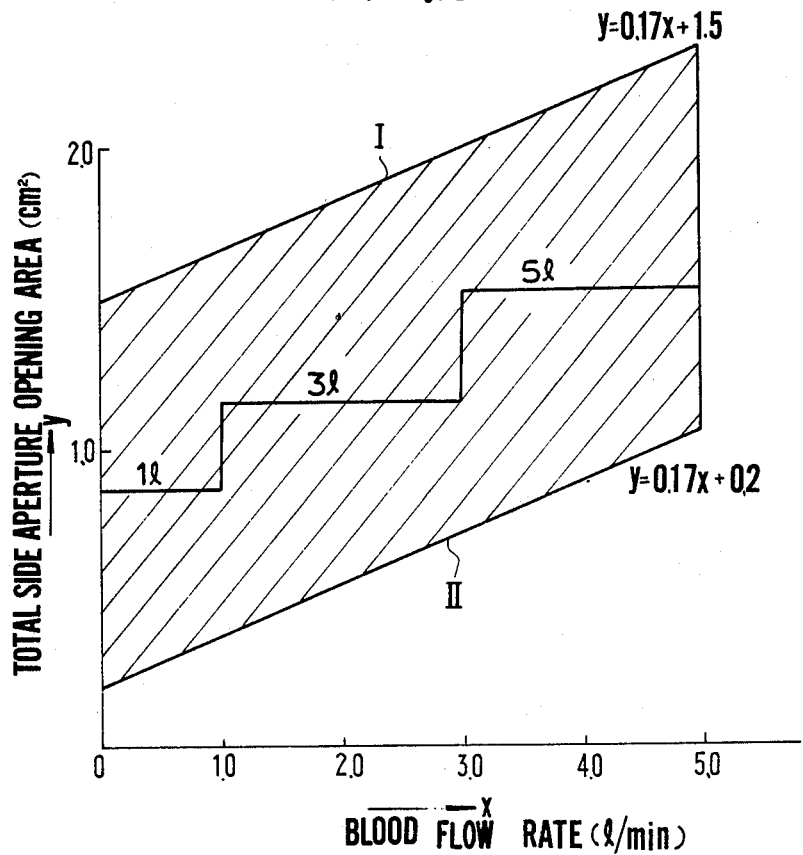

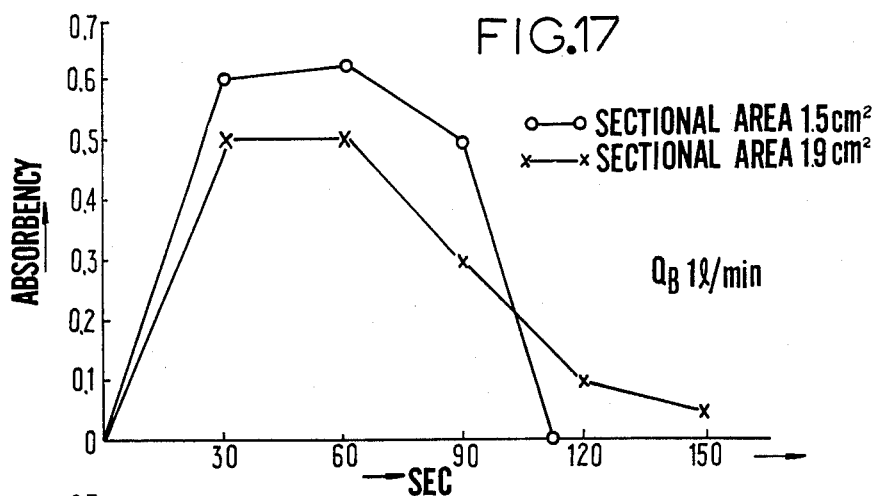
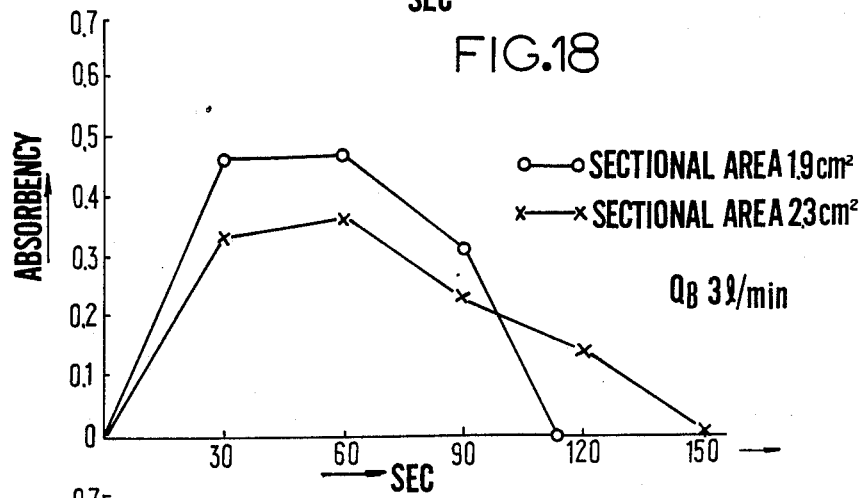
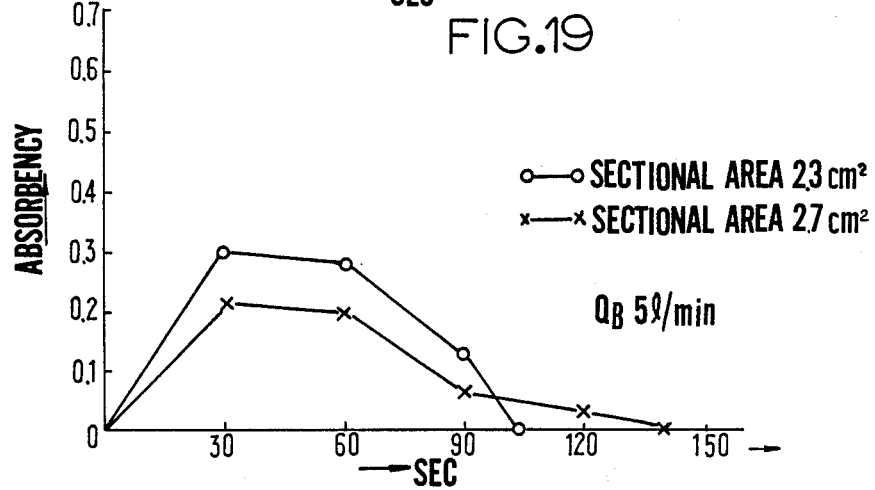

BLOOD CIRCULATING CIRCUIT FOR MEMBRANE-TYPE ARTIFICIAL LUNG, AND RESERVOIR FOR USE IN BLOOD CIRCULATING CIRCUIT

This application is a continuation of application Ser. No. 439,422, filed Nov. 5, 1982, now abandoned.

BACKGROUND OF THE INVENTION

1. Field of the Invention:

This invention relates to a blood circulating circuit for a membrane-type artificial lung. More particularly, the invention relates to a blood circulating circuit of the type described for holding the amount of extra-corporeally circulating blood within fixed limits, and to a reservoir for use in the blood circulating circuit.

2. Description of the Prior Art:

The membrane-type artificial lung features less variation in the quantity of stored blood as compared with bubble-type artificial lungs or the like, and makes it possible to gain an understanding of the amount of extra-corporeally circulating blood. However, there has not yet been developed a blood circulating circuit for a membrane-type artificial lung that can perform the foregoing with a high degree of accuracy. The blood circulating circuit of a membrane-type artificial lung generally employs a flexible reservoir for accommodating the blood that flows in an extra-corporeal circulating circuit. A flexible reservoir has the following functions, which will be described later in greater detail:

(1) to accommodate an excess of blood resulting from a variation in the extra-corporeally circulating blood of the patient, and (2) to prevent the intrusion of air into the circuit in order to protect the patient against blockage of blood vessels when there is an accidental interruption of blood flow into a tube located within a circuit for drawing the blood from the patient.

A blood circulating circuit for a membrane-type artificial lung having a flexible reservoir that possesses the above functions has been disclosed in Japanese Laid-Open Patent Publication No. 52-28195 and has the construction shown in FIG. 1. The membrane-type artificial lung used in this blood circulating circuit is of the stacked or laminated type, wherein the spacing between laminations is regulated by externally applied air pressure. In the case of a single-pump system, pressure applied to the region within the patient's body where blood is returned during extra-corporeal circulation acts upon the membrane-type artificial lung as a restitution pressure, and the spacing between the membrane layers is widened by changes in this pressure and in the pressure that prevails within the circuit, causing separation of seals and the risk of diminished gas-exchange efficiency. With the two-pump system depicted in FIG. 1, on the other hand, it becomes necessary to change the blood delivery pressure at a pump 10, as well as the blood delivery pressure at a pump 11. It is also necessary to alleviate the restitution pressure acting on a membrane-type artificial lung, designated at 14, by providing a reservoir 13. The arrangement therefore includes two reservoirs 12, 13 as well as the two pumps 10, 11. Numeral 15 denotes a heat exchanger, 16 a cardiotomy reservoir, and 17 a filter.

The above arrangement is disadvantageous in that it complicates the main circuit, shown by the bold lines, and in that it calls for an increase in the amount of priming. As shown in FIGS. 1 and 2, each of the venous reservoirs 12, 13 is constricted at its central portion by a clip 18 so that the walls of the reservoir are brought closely together, the arrangement being such that reservoir wall movement is regulated by adjusting the amount of constriction offered by the clip 18. With this design, however the movement of the wall portions not constricted by the clip cannot be regulated. As a result, there is a large variation in the internal volume, so that this scheme is not adequate for measuring the amount of extra-corporeally circulating blood. In addition, as shown by the broken lines in FIG. 2, the clip 18 forms the reservoir into a vessel which is capable of expanding freely in shape. In other words, the reservoir is converted into two interconnected vessels that are deformable or expandable freely in terms of shape, with the clip 18 being located at the center of the arrangement. However, as the venous reservoirs 12, 13 undergo deformation, such as when absorbing fluctuation in the extra-corporeal circulating conditions, it is difficult to gain an accurate understanding of the amount of blood in the circulating circuit. This means that one cannot gauge increases or decreases in the amount of blood within the patient's body, making it impossible to accurately grasp the extent of fluid loss resulting from bleeding or urination. This in turn involves the danger that correct timing for resupply blood and liquid will be lost. A further disadvantage is that the reservoir is compartmented at the portion constricted by the clip, thereby restricting the flow of blood.

As mentioned hereinabove, reservoirs such as those designated at 12 and 13 in FIG. 1 are provided in an extra-corporeal blood circulating circuit to cope with fluctuations in the amount of extra-corporeally circulating blood, that is, to increase the amount of blood delivery when there is a decrease in the amount of blood arriving from the patient, by way of example. To this end, the reservoirs function to retain a certain amount of blood within the circuit at all times. The other reason for providing the reservoirs is to effectively remove air bubbles produced within the blood circuit. Specifically, in open-heart or other surgery, air bubbles may become entrapped in the tube feeding blood from the patient if the catheter for drawing off the blood is inadequately retained within the blood vessel, or when the catheter is withdrawn therefrom. Failure to effect complete removal of air bubbles from the circuit can lead to blockage of small air vessels associated with the brain or other vital organs, thereby causing brain damage and possible loss of life. Although increasing the reservoir capacity provides a corresponding improvement in the air bubble removal effect, the greater capacity necessitates an increase in the amount of circuit priming. The result is an increase in the amount of blood transfused, with a greater possibility of post-operative hepatitis. Another reason for rejecting this expedient is the greater consumption of blood that is required.

One attempt at a solution to the above problem is disclosed in Japanese Laid-Open Utility Model Publication 55-180536. This publication proposes a reservoir in which a screen filter in the shape of a cylindrical body is disposed within a vessel, a blood inlet opens into the lower open end of the cylindrical screen filter, and the upper open end of the cylinder is directed toward a vent or deaeration port provided at the upper portion of the vessel. According to this previously disclosed reservoir, entrapped air bubbles attach themselves to the screen filter and gradually enlarge as more and more of the air bubbles become attached thereto. The air bubbles eventually separate from the screen and are removed by way of the deaeration port. The reservoir therefore exhibits an excellent air bubble removal effect and is also capable of being made small in size. When a large quantity of blood is to be drawn off from the patient, however, the blood within the reservoir develops a strong rotational or vortex-type flow. The disadvantageous result is that air bubbles are drawn into the flow and then pass into the blood outlet along with the blood.

SUMMARY OF THE INVENTION

The present invention has been devised in order to solve the aforementioned problems and to establish the surgical conditions desired in a blood circulating circuit for a membrane-type artificial lung used mainly in heart surgery.

Accordingly, an object of the present invention is to provide a blood circulating circuit for a membrane-type artificial lung wherein a fluctuation in the amount of blood in an extra-corporeal blood circulating circuit, caused by a change in circuit pressure, is held within predetermined limits.

Another object of the present invention is to provide a blood circulating circuit for a membrane-type artificial lung that enables the amount of blood within an extra-corporeal circulating circuit to be grasped with a high degree of accuracy.

Still another object of the present invention is to provide a blood circulating circuit for a membrane-type artificial lung that makes it possible to accurately grasp the amount of blood in an extra-corporeal blood circulating circuit, to maintain the circulatory conditionas best suited for the particular case and to monitor the conditions, as well as to determine the timing for resupply liquids and the like.

Yet another object of the present invention is to provide a blood circulating circuit for a membrane-type artificial lung that is easy to operate.

A further object of the present invention is to provide a reservoir, for use in the blood circulating circuit of an artificial lung, having an excellent air-bubble removal effect.

A further object of the present invention is to provide a reservoir for use in the blood circulating circuit of an artificial lung, wherein there is very little outflow of air bubbles caused by a rotational flow even when the amount of blood drawn off from the patient is very large.

According to the present invention, these and other objects are attained by providing a blood circulating circuit for a membrane-type artificial lung, comprising a sealed, flexible first reservoir communicating with a blood collecting circuit on a blood receiving side and a blood discharge circuit on a blood delivery side, a capacity restricting enclosure for restricting the first reservoir to a specified volume, and a second reservoir, disposed at a level higher than that of the first reservoir, communicating with the blood collecting circuit of the first reservoir. In a preferred embodiment of the invention, the capacity restricting enclosure restricts free deformation of the first reservoir by means of least at two opposing surfaces to substantially limit the volume of the first reservoir to a specified volume. Regulation of volume is achieved by adopting a capacity restricting enclosure which is capable of freely fixing or adjusting the clearance between surfaces for restricting the reservoir. The enclosure can be constructed as means having at least two opposing surfaces defining a space for receiving the first reservoir, and is adapted to provide a visual indication of the volume thereof. The enclosure has at least two restraining plates, each of the restraining plates having joining means for joining the plates together in an opposing relationship to restrict the capacity of the first reservoir. The enclosure can also be integrally molded into a body having two opposing surfaces.

The s;econd reservoir has means for measuring and regulating the amount of extra-corporeally circulating blood, including a graduated scale for reading a fluctation in said amount of blood. The venous pressure is regulated by adjusting the height at which the second reservoir is supported. In the preferred embodiment of the invention, the artificial lung used is of the hollow fiber type.

In another aspect of the present invention, a reservoir for the blood circulating circuit is provided. The reservoir comprises a vessel having a deaeration port provided at an upper portion thereof, blood inflow means having an end extending a predetermined distance into the vessel, which end is sealed closed, the blood inflow means having a plurality of side apertures for blood inflow into the vessel provided at a predetermined height, and blood outflow means having a blood outflow port opening into the vessel at a position lower than the side apertures. The blood outflow means is spaced away from the blood inflow means by a predetermined distance, and the blood inflow means comprises a tube whose end extending into the vessel is sealed closed, the plurality of side apertures being provided in the tube near the closed end thereof. In another embodiment of the invention, at least several of the side apertures are aligned in a row along the longitudinal axis of the tube, and a plurality of the rows of aligned side apertures are provided.

In yet another aspect of the invention, the reservoir comprises a vessel having a deaeration port provided at an upper portion thereof, blood inflow means having an end extending a predetermined distance into the vessel, which end is sealed closed, the blood inflow means having a plurality of side apertures for blood inflow into the vessel provided at a predetermined height, and blood outflow means having a blood outflow port opening into the vessel at a position lower than the side apertures. Letting the sum of the opening areas of the side apertures be represented by y (cm$^2$) and the rate of blood inflow into the vessel from the side apertures be represented by x (l/min), the blood inflow means is adapted in such a manner that the following relation is satisfied:

$$0.17x + 0.2 < y < 0.17x + 1.5$$

The blood inflow means comprises a tube, and at least two rows of the side apertures are provided extending longitudinally of the tube symmetrically with respect to the longitudinal axis thereof.

Other features and advantages of the invention will be apparent from the following description taken in conjunction with the accompanying drawings in which like reference characters designate the same or similar parts throughout the figures thereof.

BRIEF DESCRIPTION OF THE DRAWINGS

FIGS. 5A, 5B, 5C and 5D are perspective views showing modifications of an enclosure for restricting the capacity of a reservoir;

FIG. 6 is a perspective view showing yet another modification of an enclosure for restricting the capacity of a reservoir;

FIG. 7 is a perspective view showing the manner in which the free expansion of a flexible reservoir is restricted;

FIG. 8A is a perspective view illustrating a further modification of an enclosure for restricting the capacity of a reservoir;

FIG. 8B is a perspective view showing an enlargement of an engagement slot forming part of the enclosure depicted in FIG. 8A;

FIG. 8C is a perspective view showing an enlargement of a joining member forming part of the enclosure depicted in FIG. 8A;

FIG. 9 is a perspective view illustrating another modification of an enclosure for restricting the capacity of a reservoir;

FIG. 10 is a perspective view illustrating an embodiment of a reservoir according to the present invention;

FIG. 13 is a graphical representation showing a region of preferred total side aperture opening area for suitable blood flow rates, which side apertures are formed in a tube constituting a blood inflow port;

FIG. 17 is a graphical representation showing the results of an experiment conducted at a blood flow rate of 1 l/min;

FIG. 18 is a graphical representation showing the results of an experiment conducted at a blood flow rate of 3 l/min;

FIG. 19 is a graphical representation showing the results of an experiment conducted at a blood flow rate of 5 l/min;

DESCRIPTION OF THE PREFERRED EMBODIMENTS

Described first will be the construction and operation of a blood circulating circuit for a membrane-type artificial lung according to the present invention.

Construction of blood circulating circuit

Figure 3:
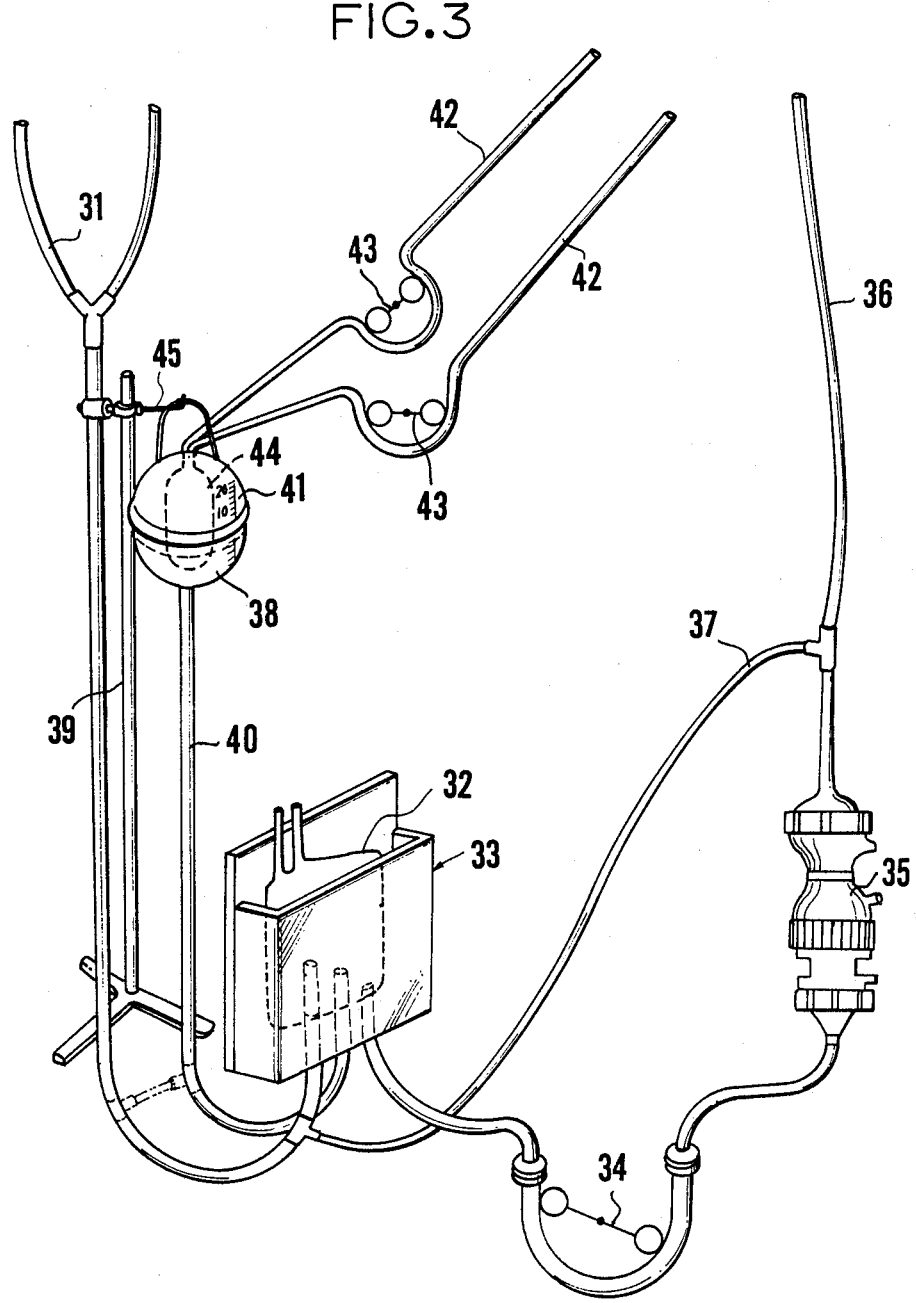
FIG. 3 is a perspective view showing the overall construction of a preferred embodiment of the present invention.

Referring to FIG. 3 illustrating the overall construction of a blood circulating circuit embodying the present invention, the circuit includes a flexible reservoir 32 to which blood drawn from the patient's vena cava during surgery is led by means of a blood collecting circuit 31 which is provided on the blood-receiving side. The blood collecting circuit 31 utilizes the vertical distance between the vena cava and the reservoir 32 to deliver the blood to the flexible reservoir 32. The flexible reservoir 32 comprises a sealed flexible vessel having ports for charging medication and for venting air during priming. The blood circulating circuit further includes an enclosure 33 for restricting the capacity of the reservoir 32. The enclosure 33 has wall members forming a compartment for receiving the reservoir 32, as shown in FIG. 3, at least two of these wall members serving to restrict the deformation of the flexible reservoir in order to set its maximum volume. A blood delivery pump 34 is connected between the flexible reservoir 32 and a membrane-type artificial lung 35, equipped with a heat exchanger, for oxygenating the venous blood from the reservoir 32, and for effecting both heat exchange and an exchange of gases to remove carbon dioxide gas from the blood. It should be noted, however, that the artificial lung and heat exchanger may be provided separately and interconnected by tubing. The venous blood drawn from the vena cava is converted into arterial blood through oxygenation achieved by passage through the membrane-type artificial lung 35. The arterial blood is then returned to the patient through a blood discharge circuit provided on the delivery side.

In view of the objects of the present invention, the membrane-type artificial lung employed in the circuit should be one which develops absolutely no fluctuation, or a negligible amount of fluctuation, in the amount of liquid within the extra-corporeal circulating circuit, the fluctuation resulting from a change in the internal circuit pressure. Accordingly, of the membrane-type artificial lungs that are available, the most preferred is a hollow-fiber membrane-type artificial lung, such as disclosed in U.S. Pat. No. 4,239,729, in which volume fluctuation due to a change in internal pressure is substantially negligible.

During circulation and priming of the artificial lung 35, the blood discharge circuit 36 on the blood delivery side is closed, circulation is effected through a circulation line 37 connecting the output side of the pump 35 with the blood collecting circuit 31, and the primed physiological salt solution, Ringer's solution, preserved blood or other medication is heated, oxygenated and gas-exchanged to remove carbon dioxide, thereby preparing blood having suitable blood gas properties. When these preparations have been completed, the blood discharge circuit 36 is opened, and the circulation line 37 is shut off from the blood collecting circuit 31 and discharge circuit 36 at the ends thereof.

The blood circulating circuit of the present invention further includes a second reservoir 38 supported by height adjusting means such as a stand 39 so that the height thereof may be adjusted freely. The second reservoir 38 is communicated with the flexible first reservoir 32 by a line 40, and is connected to the patient through the first reservoir 32 and the blood collecting circuit 31 provided on the blood receiving side. It should be noted, however, that the line 40 may be communicated with the blood collecting circuit 31 directly, as shown by the phantom lines in FIG. 3. The second reservoir 38 has a graduated scale 41 provided on its wall to permit reading of the liquid level, which indicates the amount of extra-corporeally circulating blood. Adjusting the height of the second reservoir 38 makes it possible to regulate the venous pressure of the patient.

The blood passage of the blood discharge circuit 36 on the delivery side develops a comparatively higher internal pressure than the blood passage of the blood collecting circuit 31 on the blood receiving side because of the action of pump 34. Connecting means are provided for connecting the membrane-type artificial lung 35 to the blood path of the blood discharge circuit 36. The connecting means comprises the tube ends and a member for clamping them. For example, the tubes forming the blood path are inserted into the inflow and outflow portions of the artificial lung 35 and are clamped in place by any desired clamping member that applies pressure to the tube joints. Wire may serve as the clamping member. Likewise, the means for connecting the artificial lung to the blood path of the collecting circuit 31 includes the tube ends, which are fitted together as described above, and a clamping member that applies pressure to the tube joints. If desired, however, the tubes can be fitted together without the use of a clamp.

In FIG. 3, numeral 42 denotes a suction circuit, 43 a pump, 44 a filter, and 45 a hook for suspending the second reservoir 38 from the stand 39.

Discussed next will be the details of the enclosure 33 for restricting the capacity of the flexible reservoir 32.

Figure 4A:
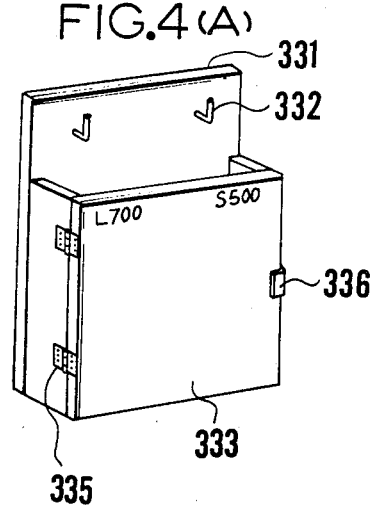
FIGS. 4A and 4B are perspective views showing an embodiment of an enclosure for restricting the capacity of a reservoir.
Figure 4B:
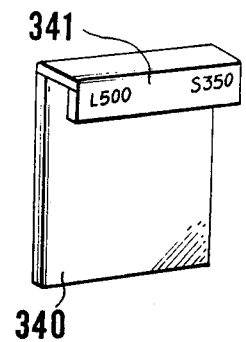

In FIG. 4A, which illustrates a typical embodiment of the present invention, the enclosure 33 for restricting the capacity of the flexible reservoir 32 comprises a box which is open at its upper and lower ends. The box has a baseboard 331 provided with L-shaped hangers 332 for suspending the flexible reservoir 32 by engaging with a flap provided on the reservoir 32, which is of the sealed, disposable type. The box-shaped enclosure further includes a cover 333 pivotally supported by hinges 335 at one edge thereof and having a lock 336 provided at the edge opposite the hinges. The two opposing walls constituted by the baseboard 331 and cover 333 delimit a space for accommodating and restricting the volume of the flexible reservoir 32. FIG. 4B illustrates an adjusting board, comprising a limiter 340 and an engaging member 341 having a volume indicating portion, for adjusting the space defined by the base board 331 and cover 333. The adjusting board is adapted to be inserted into the enclosure 33 shown in FIG. 4A, thereby reducing the size of the space or clearance between the baseboard 331 and cover 333 by the thickness of the limiter 340 to limit the expansion of the flexible reservoir 32 correspondingly. In other words, the adjusting board specifies the maximum volume of the reservoir. If flexible reservoirs 32 of two different volumes, one large and one small, are available for use, then a total of four different volumes can be specified by the limiter 340 when the adjusting board is employed. The figures L700, S500, L500, S350 shown on the cover 333 of the enclosure and on the engaging portion 341 of the adjusting board indicate the volume of the flexible reservoir 32.

Figure 5A:
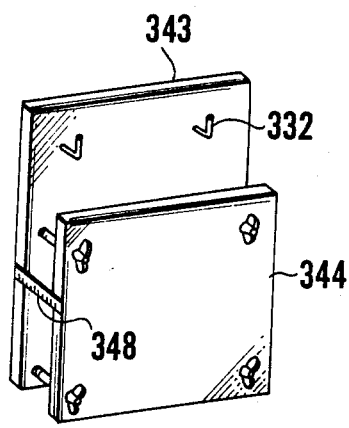
Figure 5B:
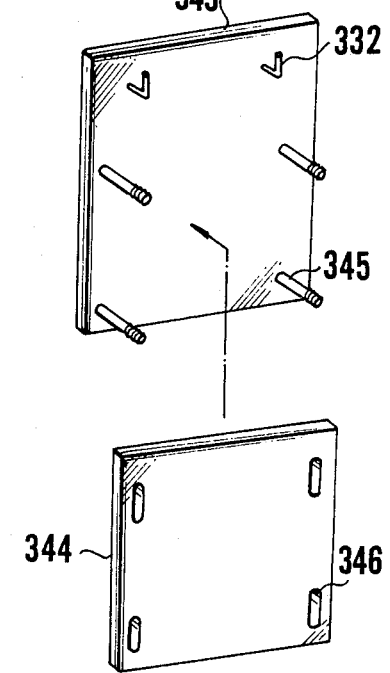

Modifications of the capacity restricting enclosure of FIG. 4 are illustrated in FIGS. 5A, 5B and 5C. Here a baseboard 343 and opposing adjusting board 344 are movable toward and away from each other to regulate the intervening space and, hence, to specify the volume of the flexible reservoir accommodated within said space. To this end, four adjustment screws 345 are affixed to the baseboard 343 for supporting the adjusting board 344 at four points, and the adjusting board 344 is provided with oblong screw holes 346 at positions corresponding to the four adjustment screws 345. Further, as shown in FIG. 5D, each adjustment screw 345 has a portion 345a which fits into the corresponding oblong screw hole 346 of the adjusting board 344, and a limiter portion 345b for regulating said fit. The adjusting board 344 is formed to include a difference in level or step 347 along the inner side of each oblong hole 346. The step 347, which has first and second levels arranged longitudinally along part of the oblong hole 346, serves to regulate the amount of penetration by the limiter portion 345b. More specifically, when the limiter portion 345b of the screw 345 does not abut against the first or second level of the step 347, the limiter portion 345b is restricted by the inner edge of the remaining portion of the oblong hole 346, that is, by the inner surface of the adjusting board 344. This corresponds to the case, described in connection with FIG. 4, where the limiter 340 is not inserted into the enclosure. When the limiter portion 345b abuts against the first or second level of the step 347, the level being selected by the attendant, the clearance between the baseboard 343 and adjusting board 344 is reduced correspondingly. The effect on the flexible reservoir 32 is the same as inserting the limiter 340 in the arrangement of FIG. 4. In FIG. 5B, the adjustment screws 345 are affixed on the baseboard 343 and the oblong holes 346 and step portions 347 are formed on the adjusting board 344. However, the same effects can be obtained by adopting the alternative shown in FIG. 5C, in which the adjustment screws 345 are affixed on the adjusting plate 344 and the oblong holes 346 and step portions 347 are formed on the baseboard 343. In either arrangement, a graduated scale 348, which bears a printed indication of the clearance between the baseboard 343 and adjusting board 344, is provided on one side of the baseboard 343 to measure the clearance and, hence, provide a reading indicative of the volume of the flexible reservoir 32.

FIG. 6 illustrates another modification of a capacity restricting enclosure according to the present invention, the enclosure comprising a baseboard 350 and a pair of side boards 351 each having an inwardly extending guide member 352 lying parallel to the baseboard 350. The baseboard 350 and side boards 351 delimit a space for accommodating the flexible reservoir 32. Also provided is a cover 353, indicated by the phantom lines, which may be slid along the inner surfaces of the opposing guide members 352 in order to be freely inserted into and withdrawn from the space defined within the enclosure. When inserted, the cover 353 cooperates with the baseboard 350 to form surfaces for limiting the expansion of the flexible reservoir 32.

It will be appreciated from FIG. 7 that the flexible reservoir 32, which is a flexible vessel that is relatively free to assume any shape, is essentially converted into a vessel of a fixed volume between the restraining surfaces P formed by the baseboard 331 and cover 333. This effect of restricting the free expansion of the vessel is enhanced by increasing the surface area of the restraining surfaces P, and by reducing the clearance c (corresponding to the allowable thickness of the vessel) between these surfaces. In other words, the effect of the large surface area and small gap is to render substantially negligible any fluctuation in vessel volume attributed to free expansion, as indicated by the dashed lines in FIG. 7.

Another modification of the capacity restricting enclosure 33 is illustrated in FIG. 8A, wherein the enclosure is capable of being constituted by molded components made of plastic. As shown in FIG. 8A, restraining plates 360, 361 are molded into substantially L-shaped configurations. To enable the restraining plates 360, 361 to be joined together slidably to allow adjustment of the intervening space, the restraining plate 360 is formed to include joining members 362 integral therewith, and the restraining plate 361 likewise is provided with joining members 363 formed integral therewith. Adjacent ones of the joining members 362 of the restraining plate 360 define engagement slots 364 between them. As shown in FIG. 8B, the opposing walls 365 of the engagement slots 364 are each formed to include positioning projections 366A, 366B which are spaced apart from each other by a predetermined distance. Further, each wall 365 is provided with a guide channel 367 extending longitudinally of the wall. A shown in FIG. 8C, in order to freely slide the joining members 363 on the restraining plate 361 into the slots 364 of the restraining plate 360 in the direction of the arrow shown in FIG. 8A, the side walls 368 of the joining members 363 are each provided with hemispherical positioning cut-outs 369 for engaging with the projections 366A, 366B on the joining members 362, and with a longitudinally extending guide rail 370 for sliding in the corresponding guide channel 367. In FIG. 8A, numerals 380 denote hooks molded on the restraining plate 360 for the purpose of suspending the sealed flexible reservoir 32 therefrom.

When using the enclosure illustrated in FIG. 8A, the flexible reservoir 32 is hung from the hooks 380, and the joining members 363 of restraining plate 361 are fit into the slots 364 of the restraining plate 360 while being guided by the guide rails 370 that fit into and slide along the guide channels 367. When the cut-outs 369 of the restraining plate 361 engage with the projections 366A nearest the entrance to each slot 364, the flexible reservoir is limited by the restraining plates 360, 361 to a capacity corresponding to a marker 700 provided on one of the joining members 362. This means that the maximum volume of the reservoir is restricted to 700 milliliters. When the joining members 363 are slid deeper into the slots 364 to bring the cut-outs 369 into engagement with the projections 366B, the restraining plates 360, 361 limit the capacity of the reservoir to the amount indicated by a marker 500 (i.e. 500 milliliters).

In FIG. 8A, characters $IN_1$, $IN_2$ printed on the left side of the restraining plate 361 indicate the inlet ports for the tube from the blood collecting circuit 31 and for the tube 40 communicating the second reservoir 38 with the sealed, flexible reservoir 32, as shown in FIG. 3. The characters OUT printed on the right side of the restraining plate 361 indicate the outlet port to the blood discharge circuit 36.

The capacity restricting enclosure illustrated in FIG. 8 can be made of molded plastic to completely eliminate the need for separately attached parts. This is conducive to mass production, and allows the capacity of the flexible reservoir to be restricted merely by adjusting one of the restraining plates relative to the other.

Reference will now be had to FIG. 9 to describe yet another modification of the capacity restricting enclosure 33, whose advantages are enhanced productivity by way of press machining, as well as improved operability. The enclosure comprises a holder 390, consisting of a unitary metal plate of aluminum or the like bent into a substantially J-shaped configuration to form opposing restraining walls 390A, 390B which define a space for receiving the sealed, flexible reservoir 32. A limiter 392, having a reinforcing rib 393, is inserted into the space between the walls 390A, 390B to reduce the amount of space available for the reservoir. Hooks 394 are formed on the wall 390a for suspending the reservoir.

In use, the reservoir 32 is suspended from the hooks 394 followed by the insertion of the limiter 392, whereby the maximum volume of the reservoir 32 is reduced by an amount corresponding to the thickness of the limiter 392.

Since the enclosure 33 is fabricated from a metal plate by means of press machining as mentioned above, a high-productivity is assured. In use, moreover, the sealed, flexible reservoir 32 need only be placed within the space delimited by the restraining walls 390A, 390B, and a reduction in the maximum volume can be achieved merely by inserting the limiter 392. The enclosure therefore is very easy to use.

It goes without saying that the operating principle of the capacity restricting enclosure 33 as described in connection with FIG. 7 applies to the arrangements of both FIGS. 8 and 9.

Operation of blood circulating circuit

Assume a condition wherein the patient's venous pressure rises due to an increase in blood delivery or because of a large quantity of resupply liquid or the like. The reservoir capacity restricting enclosure 33 having the foregoing construction, such as that illustrated in FIGS. 4A and 4B, will function to limit the expansion of the flexible reservoir 32 by means of the baseboard 331 and cover 333 (or the limiter 340 when inserted). Accordingly, once the flexible reservoir 32 has been filled with blood to a predetermined pressure, the reservoir 32 will not expand even if acted upon by a pressure in excess of the predetermined value, and will not be capable of absorbing said excess. Thus the quantity of blood forced back to the second reservoir 38 (FIG. 3) by the flexible first reservoir 32 will correspond to, or counterbalance, the increase in the center venous pressure. In other words, the liquid level of the second reservoir 38 will be commensurate with the center venous pressure (i.e., the amount of blood). The operator or attendant can read any fluctuation in the system by observing the graduations 41 provided on the second reservoir, and is therefore capable of controlling circulation to maintain a suitable center venous pressure.

Next, when there is a decrease in the amount of blood within the patient and a resulting drop in the pressure that prevails within the flexible reservoir 32, blood is transferred from the higher second reservoir 38 to the lower flexible reservoir 32 through the line 40, after which the liquid level within the second reservoir 38 stabilizes. The operator may therefore read off the decrease in the quantity of blood by observing the difference between the initial liquid level and the new liquid level following stabilization.

Effects of blood circulating circuit

According to the construction and operation of the present invention as described hereinabove, the various elements connected to the blood circulating circuit do not experience any fluctuation in liquid quantity that develops within the extra-corporeal circulating circuit owing to a change in pressure internally of the circuit. It is therefore possible to hold the amount of blood within the blood circulating circuit constant, and to achieve the desired circuit conditions. In addition, any fluctuation in the amount of extra-corporeally circulating blood can be read as a change in the liquid level of the second reservoir 38, making it possible to carry out circulation and liquid resupply reliably and at the required timing. In the preferred embodiment of the invention, the second reservoir 38 can be changed in position to vary the liquid level, thereby enabling the venous pressure to set to any desired value.

In the preferred embodiment of the invention as described and illustrated hereinabove, the artificial lung incorporates the heat exchanger. It is permissible, however, to provide these components separately and then connect them to the blood collecting circuit on the blood receiving side. Furthermore, two pumps can be provided and connected to the reservoir restricted in thickness by means of the capacity restricting enclosure.

Construction of Reservoir

Figure 11:
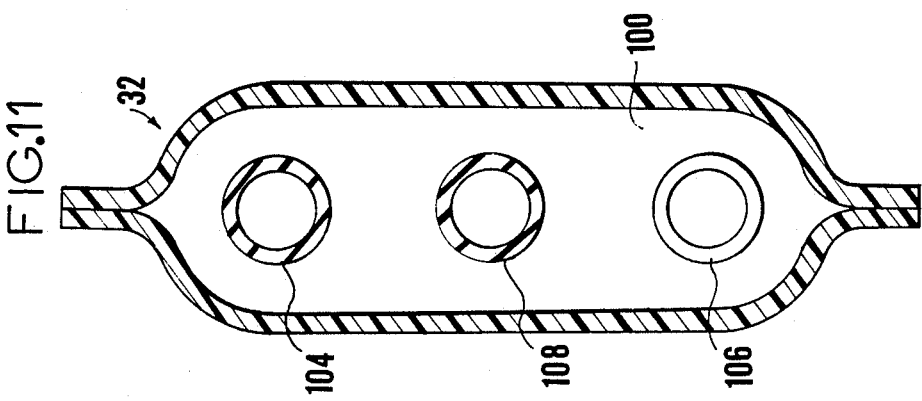
FIG. 11 is a sectional view taken along the line XI—XI of FIG. 10.

Reference will now be had to FIGS. 10 and 11 to describe the construction of a reservoir 32 capable of being used in a blood circulating circuit for artificial lungs of membrane type. The reservoir 32 comprises a vessel 100 made of a flexible or rigid material. The material should be one which does not affect the properties of blood and which does not contain elutants. Suitable materials for use are those that are compatible with blood, such as silicone rubber, polyvinyl chloride, polycarbonate, and ethylene vinyl acetate copolymer. In the embodiment to be described hereinafter, the vessel 100 is made of a flexible material and has the form of a bag or pouch, as illustrated in the drawings. The interior of the vessel is devoid of air despite changes in the amount of blood retained therein, the amount of retained blood being determined by the expansion of the vessel. The vessel thus minimizes any degradation of blood albumin or the like attributed to contact between blood and air.

The upper portion of the vessel 100 is formed to include deaeration ports 102, 102 for removing air bubbles that separate and float up from the blood within the vessel. The ports 102, 102, of which two are provided in the illustrated embodiment, may also serve as openings for sampling and for charging liquids. The vessel 100 is further provided with a blood inflow port 104 for communicating the blood collecting circuit 31 (FIG. 3) with the interior of the vessel, and with a blood outflow port 106 which communicates the interior of the vessel with the artificial lung 35 for leading blood into the artificial lung. The blood inflow port 104 and blood outflow port 106 are spaced away from each other by a predetermined distance. Also provided on the vessel 100 is a communicating port 108 leading to the line 40 for communicating the second reservoir 38 with the first reservoir 32 whenever necessary. The ports 104, 106, 108, which are tubular in shape, are disposed at the bottom portion of the vessel 100 and extend into the interior thereof.

The tubular blood inflow port 104 preferably is provided with two or more apertures at the portion thereof extending into the vessel 100. These apertures serve to minimize the development of rotational or vortex flow in the entrant blood, and cause plural rotational blood streams to cancel one another. In order to prevent the air bubbles contained in the entrant blood from being drawn into the flow of exiting blood, the blood inflow port 104 and blood outflow port 106 are spaced apart by a predetermined distance of 56 mm between central longitudinal axes, by way of example. The air bubbles are further prevented from remaining entrapped in the entrant blood by positioning the side apertures 110 at a level higher than the opening formed in the end of the blood outflow port 106. The above construction is essential to realize the full air bubble removing effect of the invention; merely forming the blood inflow port 104 into a straight tube with an open end will not suffice. To provide the apertures in the inflow port 104, some of the available expedients are to form the tubular inflow port into a number of branches, or to form the end of the tube into a sprinkler-like configuration. For the sake of manufacturing facility and to assure a sufficient quantity of blood inflow, however, the preferred arrangement is that the inflow port 104 comprise a tubular body whose end portion within the vessel 100 is sealed closed, and that a plurality of side apertures 110, 110 be formed in the tubular port near the sealed end thereof.

The side apertures 110 formed in the walls of the blood inflow port 104 whose upper end is sealed closed may be arranged in a variety of ways, and a number of aperture shapes are possible. For example, the apertures 110 may be circular or elliptical in shape to facilitate the outflow of the blood, and a multiplicity thereof may be provided. A preferred arrangement of the apertures in such case is one which is cable of moderating the energy possessed by the flowing blood. The most preferred arrangement is to provide at least two longitudinally extending rows of the side apertures 110 symmetrically with respect to the longitudinal axis of the tubular inflow port. A typical arrangement of this type is shown in FIG. 10, illustrating longitudinally extending rows of the side apertures 110 formed in the tube constituting the blood inflow port 104.

Figure 12C:
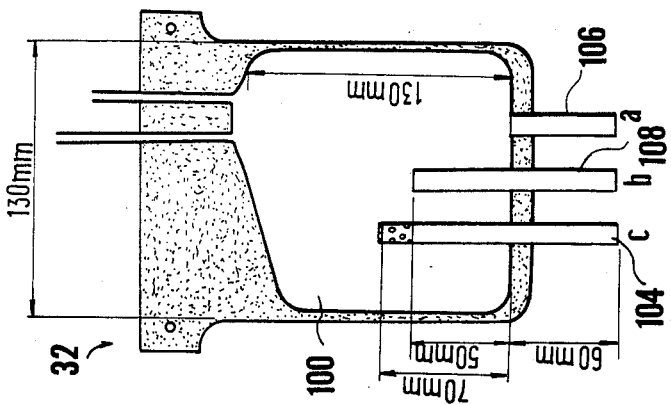
FIGS. 12A, 12B and 12C are sectional views illustrating three examples of reservoirs according to the present invention along with the associated inlet, outlet and communication ports, for describing the dimensions of the reservoirs and the preferred relative locations of said ports.
Figure 12B:
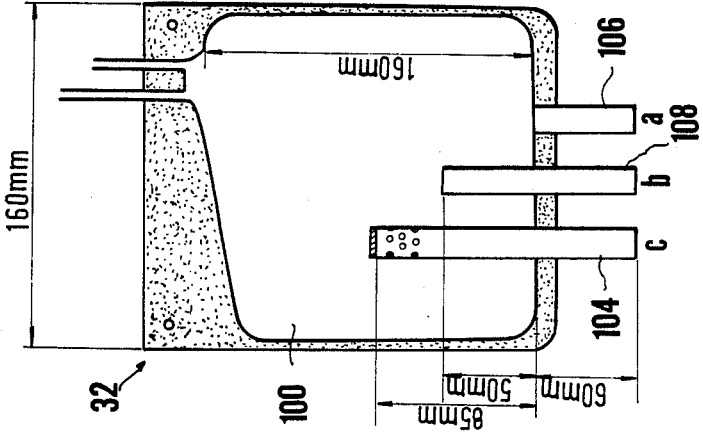
Figure 12A:
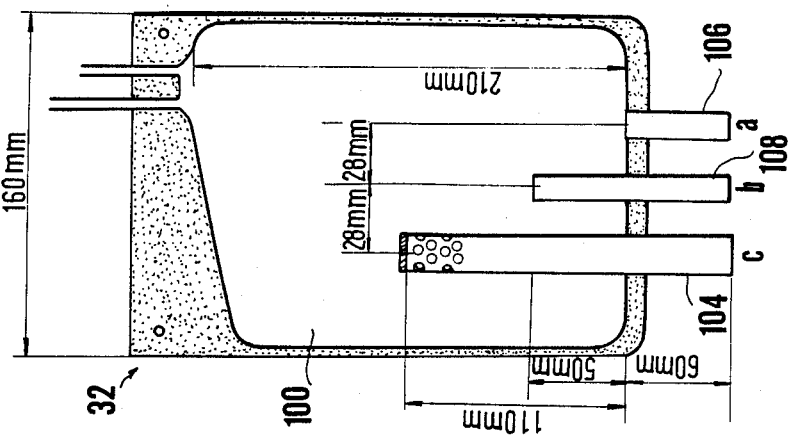

FIGS. 12A, B and C show preferred arrangements for the blood inlet and outlet ports 104, 106 in the vessel, specifically the height of the inlet 104 from the bottom of the vessel and the spacing between the inlet port 104 and outlet port 106. In the following table 1, L, M and S stand for reservoirs of large, medium and small volume, respectively. The first, second and third stages of reservoir content are attained by restricting a reservoir of a given volume to three different capacities using the capacity restricting enclosures illustrated in FIGS. 4, 5, 8, etc.

TABLE I

| type | Tube Diameter (mm) a | b | c | No. of side aperture in blood inlet tube | Height of blood inlet from reservoir bottom (mm) | *Reservoir content (ml) First stage | Second stage | Third stage | Circulation (l/min) |
|---|---|---|---|---|---|---|---|---|---|
| L | 10 | 10 | 12.5 | 16 | 110 | 520 | 720 | 920 | 3 or more |
| M | 8 | 10 | 10 | 12 | 85 | 370 | 500 | 650 | 1 to 3 |
| S | 6 | 8 | 8 | 8 | 70 | 240 | 305 | 370 | up to 1 |

*reservoir content at 25 C

Research has been conducted into the matter of the total area possessed by the side apertures 110, as well as the influence the total area has upon blood flow. Letting the sum of the aperture areas be y (cm$^2$) and the blood flow rate through the blood inflow port 104 be x (l/m), y should satisfy the following relation to provide the best results:

$$0.17x + 0.2 \leq y \leq 0.17x + 1.5 \quad (1)$$

A graphical representation of the foregoing is illustrated in FIG. 13. How Eq. (1) was obtained will now be described in detail.

First, it should be noted that reducing the opening area of the side apertures diminishes the flow rate of the blood drawn off from the surgical field. On the other hand, overly enlarging the opening area weakens the flow energy of the blood within the reservoir to an excessive degree, causing blood to remain within the reservoir rather than flowing out through the outflow port. The following experiment was conducted to find the optimum side aperture opening area.

(1) Determination of minimum opening area for assuring collection of blood from surgical field.

The reservoir used in this case was a polyvinyl chloride bag having dimensions of about 160×170 mm. The total side aperture opening area was changed by using identical bags whose blood inlet ports were provided with different numbers of the side apertures in each run of the experiment.

Method

Figure 14:
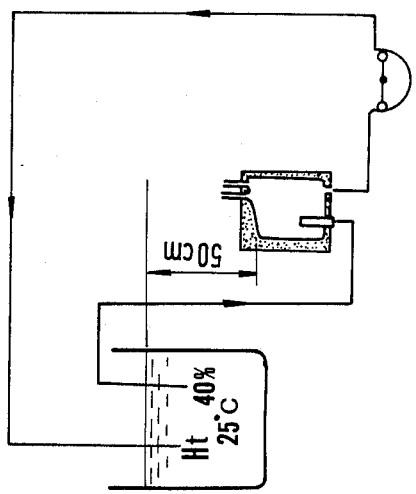
FIG. 14 is a diagram of a fluid circuit for determining minimum side aperture opening area for the purpose of assuring a proper blood collecting flow rate.
Figure 15:
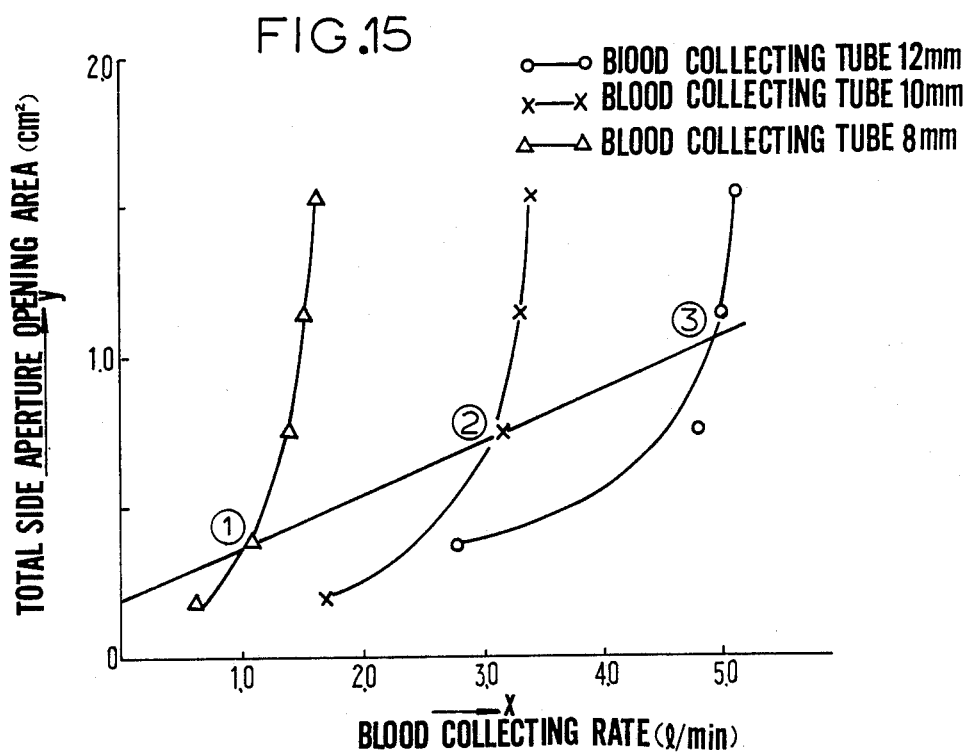
FIG. 15 is a graphical representation showing the results of experiments performed using the circuit of FIG. 14.

The experiment was conducted using the circuit arrangement shown in FIG. 14. Heparin-added cow's blood was used, Ht 40%, with the temperature adjusted to 25° C. The difference in level between the reservoir and the liquid level of the heparin solution was 50 cm. Using reservoirs having different numbers of the side apertures in the respective blood inlet ports thereof, the blood solution was circulated through the circuit of FIG. 14 and the deaeration ports at the top of the reservoir were opened. The number of pump revolutions, read when the liquid level of the reservoir stabilized, was taken as indicating the blood collection rate from the surgical field. The results are as shown in the graph of FIG. 15, in which the blood collection flow rate (x) is plotted along the horizontal axis and the sum (y) of the side aperture opening areas is plotted along the vertical axis. Furthermore, the symbols Δ indicate measurements pertaining to a blood collecting tube diameter of 8 mm. Similarly, the symbols x and o indicate measurements pertaining to blood collecting tube diameters of 10 and 12 mm, respectively.

Results

FIG. 15 clearly shows that in order to obtain a flow rate of no less than 1 l/m with a blood collecting tube having an inner diameter of 8 mm, the side aperture opening area should be no less than the value at point (1). Similarly, with an inner diameter of 10 mm, the side aperture opening area should be no less than the value at point (2) to obtain a flow rate of no less than 3 l/m and, with an inner diameter of 12 mm, the required side aperture opening is no less than the value at point (3) to obtain a flow rate of no less than 5 l/m. Note also that opening areas having values falling below the indicated points may cause part of the solution to reside within the reservoir. Deriving the recurrence formula of points (1), (2) and (3) gives the expression $y > 0.17x + 0.2$.

(2) Determination of maximum opening area for preventing residence of blood

The reservoir employed was the same as that described in (1) above.

Method

Figure 16:
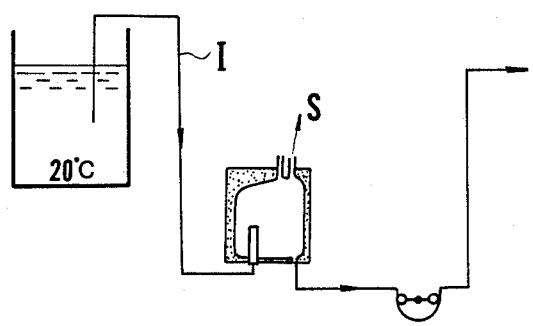
FIG. 16 is a diagram of a fluid circuit for determining maximum side aperture opening area for the purpose of preventing prolonged residence of blood within a reservoir.

The experiment was conducted based on a pigment dilution method using the circuit arrangement of FIG. 16. Specifically, water was passed through the circuit at a predetermined flow rate, and 10 cc of a pigment (an aqueous alkaline soluton of BSP, namely bromo-sulfonphthalein) was introduced in one shot from line I in FIG. 16. At five points in time thereafter, namely 30, 60, 90, 120 and 150 seconds after the injection of BSP, the solution within the reservoir was sampled from a deaeration tube S and subjected to a light absorbency measurement using a colorimeter. It should be noted that the reservoir was placed in a plate-type holder to restrict its capacity to 150, 350 and 500 ml at flow rates of 1 l/min, 3 l/min and 5 l/min, respectively.

Results

Figure 20:
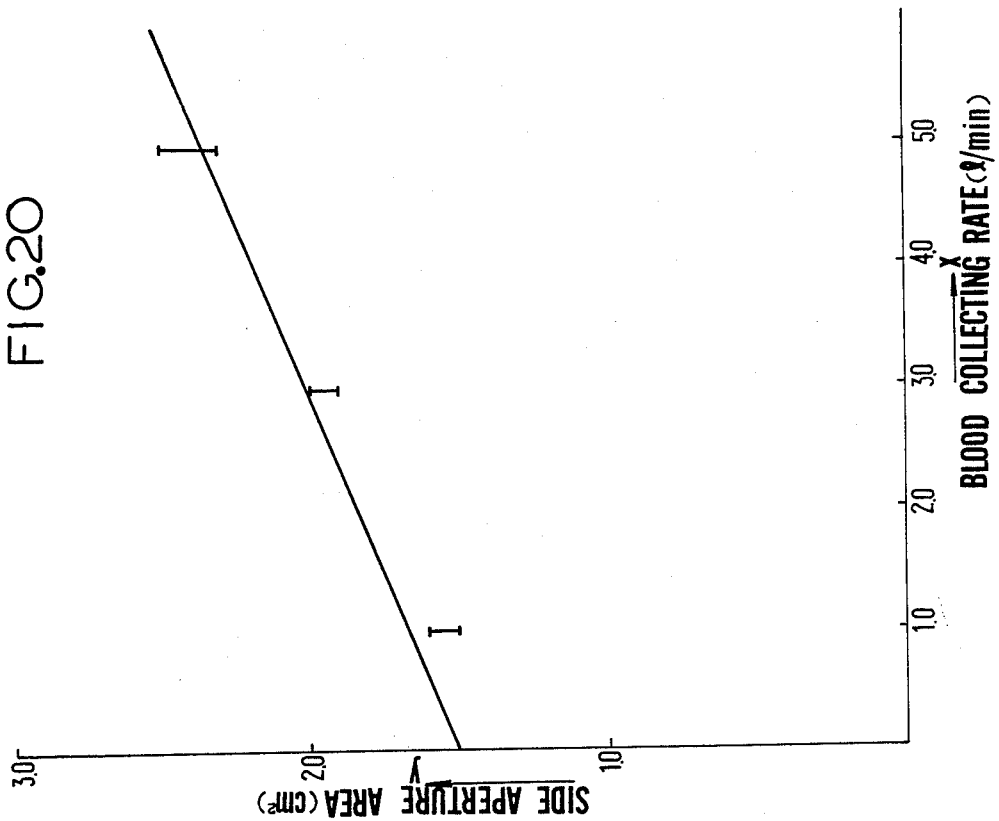
FIG. 20 is a graphical representation for finding the optimum side aperture opening area from the experimental results shown in FIGS. 17 through 19.

The results for flow rates of 1 l/min, 3 l/min and 5 l/min are as shown in FIGS. 17, 18 and 19, respectively. FIG. 17 indicates that the pigment vanishes within 120 seconds with an opening area of 1.5 cm$^2$ at a flow rate of 1 l/min, but that the pigment is still detectable at 150 seconds with an opening area of 1.9 cm$^2$ for the same flow rate. This demonstrates residence of the pigment within the reservoir. Taking the 120 second mark as a point of reference, therefore, the optimum side aperture opening area for the flow rate of 1 l/min is between about 1.5 and 1.6 cm$^2$. Similarly, the optimum side aperture opening area was found to be between 1.9 and 2.0 cm$^2$ for the flow rate of 3 l/min, and between 2.3 and 2.5 cm$^2$ for the flow rate of 5 l/min. Plotting the optimum side aperture opening areas for the above three flow rates gives the curve shown in FIG. 20. Deriving the recurrence formula gives the expression $y < 0.17 + 1.5$.

It may be understood from the experimental results that the preferred side aperture opening area falls within the region bounded by the two straight lines I, II in FIG. 13. It should be noted that the flow rate is above zero within the bounded region, and that 5 l/min is taken as the upper limit since this is generally deemed to be sufficient. However, 5 l/min need not necessarily be the upper limit on the flow rate. In connection with Eq. (1) given above, a total opening area in the region above the straight line I in FIG. 12 will cause blood to remain within the reservoir and thus result in poor blood circulation therethrough. If the total opening area of the side apertures is in the region below the straight line II, on the other hand, it will not be possible to obtain the prescribed flow rate from the surgical field.

The communicating port 108 and blood outflow port 106, so provided as to communicate with the interior of the vessel 100, may be of the ordinary tubular type whose end portions within the vessel are open. Depending upon how the reservoir 32 is used, the communicating port 108 may serve as means for communicating the vessel 100 with a carditomy reservoir for absorbing, storing or removing blood from the surgical field, or for communicating with another reservoir (such as the first or second reservoir 12 or 13 shown in FIG. 1) in a two-pump system. One or more of the ports 108 can be provided.

Operation of reservoir

Figure 1:
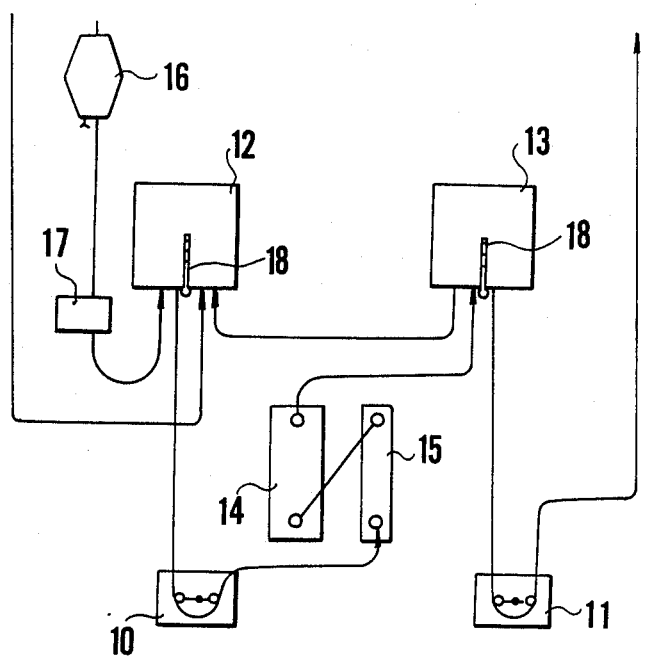
FIG. 1 is a block diagram illustrating a conventional two-pump blood circulating circuit for a membrane-type artificial lung.
Figure 2:
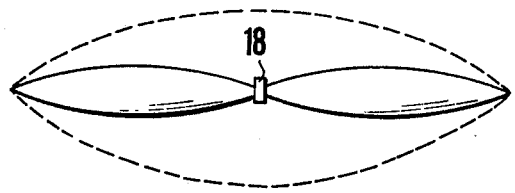
FIG. 2 is a sectional view illustrating the free deformation of a venous reservoir shown in the block diagram of FIG. 1.

The reservoir of the present invention may be employed as either of the first and second reservoirs 12, 13 in the two-pump system of FIG. 1, or as the reservoir 32 in the single-pump system of FIG. 3. In operation, blood entering from the blood inflow port 104 is split into a multiplicity of streams within the vessel 100 constituting the reservoir 32, by the action of the apertures 110. The streams or currents of blood have a multiplicity of directions depending upon the number and disposition of the side apertures 110. However, in a case where at least two longitudinally extending rows of the side apertures 110 are provided below the sealed end of the tubular inflow port symmetrically with respect to the longitudinal axis of the tube, as illustrated in FIG. 10, the divided streams, which are directed radially of the tube, exhibit a reduced flow rate so that convection currents do not readily develop and there is some mitigation of the flow energy. This promotes the separation and removal of air bubbles from the blood. Moreover, since the design is such that the total opening area of the side apertures falls within the shaded region of FIG. 13, the desired rate of blood collection from the surgical field is assured without some of the entrant blood remaining within the vessel 100. Thus, by introducing the blood into the vessel 100 from the side apertures 110 of the inflow port 104 in the manner described, air bubbles contained in the gentle flow of blood, which is free of convection currents, float up to the top of the vessel where they exit from the deaeration ports 102. As a result, the blood exiting via the blood outflow port 106 is extremely low in the quantity of entrapped air bubbles.

The inventor has performed an experiment using the set-up shown in FIG. 21 in order to confirm the actions and effects of the reservoir according to the present invention as described hereinabove. The experimental results are as shown in Table I.

Figure 21:
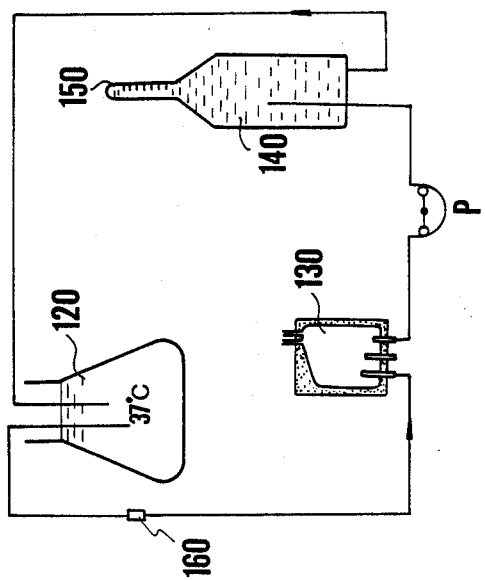
FIG. 21 is a fluid circuit for an experimental set-up for the purpose of confirming the actions and effects of the present invention.

Referring to FIG. 21, numeral 120 denotes a flask containing blood, 130 a reservoir, 140 an air trap, 150 a graduated air reservoir, and 160 an air injection device.

Two reservoirs 130 were prepared constituting a vessel consisting of a flexible polyvinyl chorlide bag having dimensions of 160×170 mm, as shown in FIGS. 10 and 11. One reservoir (No. 1 in Table I) for the purpose of comparison was provided with a straight tube, having an open end and a diameter of 10 mm, as the blood inflow port 104. The other reservoir (No. 2 in Table I), conforming to the present invention, was provided with a blood inflow port in the form of a tube having a closed end and 16 side apertures symmetrically disposed in four rows, for a total aperture opening area of 1.54 cm$^2$. Using heparin-added cow's blood at a temperature of 37° C., the blood was introduced from the flask 120 into both the comparison reservoir and the reservoir of the invention and then circulated by means of a blood pump P. Both reservoirs were disposed at the same level below the level of the flask 120. Air was injected into the circuit at a rate of 30 ml/min for five minutes (for a total of 150 ml) by means of a syringe in the air injecting device 160. Thereafter, the amount of air which had collected in the air reservoir 150 of the air trap 140 was measured. This was done at blood flow rates of 3, 4 and 5 l/min.

It will be appreciated from the results of Table 2 that the amount of air collected in the air trap 140, namely the amount of air which exits from the blood outflow port of the reservoir 130, is much less for the present invention in comparison with the conventional reservoir having the straight tube with the open end.

TABLE II

| Blood flow rate | 3 l/min | 4 l/min | 5 l/min |
| --- | --- | --- | --- |
| Reservoir No. 1 (Comparison) | 6.0 cc | 7.0 cc | 8.5 cc |
| Reservoir No. 2 (This Invention) | 0.5 cc | 1.0 cc | 2.0 cc |

Effects of reservoir

The reservoir according to the present invention exhibits a very high air bubble removing effect through a very simple construction wherein the side openings for blood inflow formed in the blood inflow means incorporated within the reservoir are positioned at a level higher than the outlet of the blood outflow means. Spacing the blood inflow means away from the blood outflow means by a prescribed distance prevents air bubbles from being drawn into the exiting blood and further enhances the air bubble removing effect. In a case where at least two longitudinally extending rows of the side apertures are provided below the sealed end of the tubular inflow port symmetrically with respect to the longitudinal axis of the tube, the divided streams of blood flow out radially symmetrically with respect to the tubular inflow port and promote air bubble removal. Furthermore, whereas the prior art required the installation of an air trap in the blood delivery line to ensure safety, the present invention does away with the air trap and hence minimizes the amount of priming needed. Moreover, by adopting the total side aperture opening area and the blood inflow rates according to the present invention, blood will not remain within the reservoir and the desired blood collecting flow rate can be assured. The blood returned to the patient will be almost completely free of air bubbles.

As many apparently widely different embodiments of the present invention can be made without departing from the spirit and scope thereof, it is to be understood that the invention is not limited to the specific embodiments thereof except as defined in the appended claims.

What we claim is:

1. An extra-corporeal blood circulating circuit, comprising:
    a hollow-fiber membrane-type artificial lung in which volume fluctuation in the artificial lung due to a change in internal pressure in the artificial lung is substantially negligible;

a sealed, flexible first reservoir communicating with at least a blood collecting circuit on a blood receiving side of the artificial lung and a blood discharge circuit on a blood delivery side of the artificial lung, said first reservoir being deformable;

a capacity restricting enclosure for said first reservoir for adjustably restricting the capacity of said first reservoir, said capacity restricting enclosure having:

at least two opposing spaced apart plate members between which said first reservoir is disposed;

slideable engaging means coupled to said opposing plate members for permitting an opposing plate member to be selectively movable relative to another of said opposing plate members to selectively vary the spacing or clearance therebetween; and fixing means for fixing the position of said movable plate member relative to said another plate member as set by said slideable engaging means to fixedly set the spacing or clearance between said opposing plate members in order to cause said first reservoir always to contain the same limited and fixed predetermined selectable maximum volume of blood during circulation of blood through the blood circulating circuit;

a second, non-deformable reservoir;

communicating means for selectively communicating said second reservoir with said first reservoir;

said second reservoir including a transparent vessel for measuring and adjusting the amount of extra-corporeal circulating blood and indicating means attached to the transparent vessel for indicating the level of blood contained therein;

supporting means for adjustably supporting said second reservoir at a level higher than that of an uppermost edge of said first reservoir, and capable of adjusting said level of said second reservoir; and means for supplying blood under pressure from said artificial lung to said first reservoir to cause said first reservoir to expand to said limited and fixed predetermined selectable maximum volume as defined by said capacity restricting enclosure so that said first reservoir is filled with said supplied blood and maintained at said limited and fixed predetermined selectable maximum volume, and blood from said first reservoir, responsive to an increase in blood pressure in said first reservoir after said first reservoir is filled to said selectable maximum volume, being forced to flow through said communicating means up to said second reservoir, the quantity of blood forced up to said second reservoir corresponding to said increase in blood pressure in said first reservoir, so that the level of blood in said second reservoir as indicated by said indicating means indicates the amount of blood circulating in the extra-corporeal blood circulating circuit.

2. The blood circulating circuit according to claim 1, in which said capacity restricting enclosure comprises a receiving member having said opposing plate members and said limiting means, and defining a space for receiving said first reservoir.

3. The blood circulating circuit according to claim 1 in which said capacity restricting enclosure includes means for providing a visual indication of the limited predetermined volume of said first reservoir.

4. The blood cirulating circuit according to claim 1, in which said capacity restricting enclosure comprises a receiving member for receiving said first reservoir, said receiving member having at least said two opposing plate members which form opposed surfaces of said capacity restricting enclosure, each of said plate members having joining means for joining said plate members together in an opposing relationship to restrict the maximum capacity of said first reservoir.

5. The blood circulating circuit according to claim 1, in which said indicating means of said second reservoir includes graduations for reading a fluctuation in the amount of extra-corporeally circulating blood.

6. The blood circulating circuit according to claim 1 wherein said means for supplying blood under pressure includes a pump coupled to said first reservoir.

7. An extra-corporeal blood circulating circuit comprising:

a hollow fiber membrane-type artificial lung in which volume fluctuation in the artificial lung due to a change in internal presssure in the artificial lung is substantially negligible; p1 a sealed, flexible first reservoir communicating with at least a blood collecting circuit on a blood receiving side of the artificial lung and a blood discharge circuit on a blood delivery side of the artificial lung, said first reservoir being deformable.

said first reservoir comprising a deformable vessel having at least one deaeration port provided at an upper portion thereof, blood inflow means having an end extending a predetermined distance into said vessel and defining an outlet interior of said vessel, and blood outflow means having a blood outflow port opening into said vessel at a position lower than said outlet of said blood inflow means;

a capacity restricting enclosure for said first reservoir for adjustably restricting the capacity of said first reservoir so that said first reservoir always contains the same limited and fixed predetermined selectable maximum volume of blood during circulation of blood through the blood circulating circuit;

said capacity restricting enclosure having at least two opposing spaced apart surfaces with said first deformable reservoir interposed therebetween, one of said opposing surfaces of said capacity restricting enclosure being selectively movable relative to the other of said opposing surfaces to selectively vary the spacing therebetween, and said opposing surfaces of said capacity restricting enclosure respectively engaging opposing major surfaces of said first deformable reservoir for limiting expansion of said first deformable reservoir in at least two dimensions to define said limited and fixed predetermined selectable maximum volume;

said capacity restricting enclosure further including fixing means for fixing the position of said movable opposing surface relative to said other of said opposing surfaces at a selectively set position to thereby fixedly set the spacing between said opposing surfaces in order to cause said first deformable reservoir always to contain the same limited and fixed predetermined selectable maximum volume of blood during circulation of blood through the blood circulating circuit;

a second, non-deformable reservoir;

communicating means for selectively communicating said second reservoir with said first reservoir;

said second reservoir including a transparent vessel for measuring and adjusting the amount of extra-corporeal circulating blood and indicating means attached to the transparent vessel for indicating the level of blood contained therein;

supporting means for adjustably supporting said second reservoir at a level higher than that of an uppermost edge of said first reservoir, and capable of adjusting said level of said second reservoir; and means for supplying blood under pressure from said artificial lung to said first reservoir to cause said first reservoir to expand to said limited and fixed predetermined selectable maximum volume as defined by said capacity restricting enclosure so that said first reservoir is filled with said supplied blood and maintained at said limited and fixed predetermined selectable maximum volume, and blood from said first reservoir, responsive to an increase in blood pressure in said first reservoir after said first reservoir is filled to said selectable maximum volume, being forced to flow through said communicating means up to said second reservoir, the quantity of blood forced up to said second reservoir corresponding to said increase in blood pressure in said first reservoir, so that the level of blood in said second reservoir as indicated by said indicating means indicates the amount blood circulating in the extra-corporeal blood circulating circuit.

8. The blood circulating circuit according to claim 7, wherein the end of said blood inflow means is sealed closed and the blood inflow means has a plurality of side apertures for blood inflow into said vessel.

9. The blood circulating circuit according to claim 7, wherein said means for supplying blood under pressure includes a pump coupled to said first reservoir.

10. The blood circulating circuit according to claim 7, in which said indicating means of said second reservoir includes graduations for reading a fluctuation in the amount of extra-corporeally circulating blood.

* * * * *

UNITED STATES PATENT AND TRADEMARK OFFICE
CERTIFICATE OF CORRECTION

PATENT NO. : 4,765,959
DATED : August 23, 1988
INVENTOR(S) : H. Fukasawa

It is certified that error appears in the above-identified patent and that said Letters Patent is hereby corrected as shown below:

Column 3, line 33, "conditionas" should be --conditions--.

Column 3, line 62, "at" should be deleted.

Column 18, line 24 (Claim 7), "pl" should be deleted. Also, new paragraph should be at "a sealed,..." in the same line.

Signed and Sealed this

Twenty-eighth Day of February, 1989

Attest:

DONALD J. QUIGG

Attesting Officer    Commissioner of Patents and Trademarks